United States Patent
Cannon

(10) Patent No.: US 6,580,501 B2
(45) Date of Patent: Jun. 17, 2003

(54) APPARATUS AND METHOD FOR THE VISUAL INSPECTION IN PARTICULAR OF CONCEALED SOLDERED JOINTS

(75) Inventor: Mark Cannon, Karlsruhe (DE)

(73) Assignee: Ersa GmbH (DE)

( * ) Notice: Subject to any disclaimer, the term of this patent is extended or adjusted under 35 U.S.C. 154(b) by 0 days.

(21) Appl. No.: 09/866,400

(22) Filed: May 25, 2001

(65) Prior Publication Data

US 2001/0024273 A1 Sep. 27, 2001

Related U.S. Application Data

(63) Continuation of application No. 09/394,732, filed on Sep. 13, 1999, now abandoned.

(30) Foreign Application Priority Data

Oct. 19, 1998 (DE) .......................................... 198 47 913

(51) Int. Cl.[7] .............................................. G01N 21/00
(52) U.S. Cl. ................................ 356/237.1; 356/237.5; 356/241.4; 359/798
(58) Field of Search ................ 356/237.1, 237.2–237.5, 356/394, 241.4, 241.1; 348/124, 65; 382/150; 29/833; 359/368, 369, 373, 385, 387, 389, 798, 802, 726, 882; 600/171, 173

(56) References Cited

U.S. PATENT DOCUMENTS

| 3,279,460 A | * | 10/1966 | Sheldon |
| 4,277,168 A | * | 7/1981 | Oku ........................... 356/138 |
| 4,686,565 A | * | 8/1987 | Ando ........................... 358/101 |
| 4,727,859 A | * | 3/1988 | Lia ............................... 128/6 |
| 4,846,154 A | | 7/1989 | MacAnalley et al. |
| 5,052,802 A | * | 10/1991 | Hayes et al. ................. 356/237 |
| 5,170,775 A | * | 12/1992 | Tagami ........................... 128/4 |
| 5,613,936 A | * | 3/1997 | Czarnek et al. ............. 600/166 |
| 5,644,438 A | * | 7/1997 | Pottash ........................ 359/798 |
| 6,023,368 A | * | 2/2000 | Woo et al. ................... 359/387 |

FOREIGN PATENT DOCUMENTS

| DE | 7440701 | 4/1975 |
| DE | 28 01 146 | 7/1978 |
| DE | 42 07 874 A1 | 9/1993 |
| DE | 43 04 422 C1 | 7/1994 |
| DE | 296 03 327 U1 | 5/1996 |
| DE | 298 05 624 U1 | 7/1998 |
| DE | 298 06 922 U1 | 7/1998 |
| DE | 198 30 710 A1 | 2/1999 |
| JP | 3-215704 | 9/1991 |
| JP | 4-47255 | 2/1992 |
| JP | 4-230720 | 8/1992 |
| JP | 6-94429 | 4/1994 |
| JP | 6-244600 | 9/1994 |

OTHER PUBLICATIONS

ELTROTEC Elektro–GmbH Sep. 1995 *Technische Endoskopie Für Den Industriellen Einsatz.*
Richard Wolf GmbH *Wolf–Lula.*

* cited by examiner

Primary Examiner—Hao Q. Pham
(74) Attorney, Agent, or Firm—McGlew and Tuttle, P.C.

(57) ABSTRACT

An apparatus for the visual inspection in particular of concealed soldered joints is provided, in particular between an electric or electronic component disposed on the surface of a printed circuit board and the printed circuit board. The apparatus includes with an ocular unit, a lens head, an image transmission unit for transmitting the image received by the lens head to the ocular unit and an illuminating device for illuminating the soldered joints to be tested. The lens head includes a device for image deviation which extends up to the axially outer end of the lens head, and in which the illuminating device is disposed in the lens head in such a way that the exit angle of the light of the illuminating device out of the lens head is substantially equal to the deviation angle of the image deviation. The exit point of the light is disposed next to the device for image deviation in the area of the axially outer end of the lens head.

28 Claims, 3 Drawing Sheets

APPARATUS AND METHOD FOR THE VISUAL INSPECTION IN PARTICULAR OF CONCEALED SOLDERED JOINTS

RELATED APPLICATIONS

This is a Continuation of application Ser. No. 09/394,732 filed Sep. 13, 1999 now abandoned, and the entire disclosure of this prior application is considered to be part of the disclosure of the accompanying application and is hereby incorporated by reference therein.

FIELD OF THE INVENTION

The invention relates to an apparatus for the visual inspection in particular of concealed soldered joints, in particular between an electric or electronic component disposed on the surface of a printed circuit board and the printed circuit board.

BACKGROUND OF THE INVENTION

In the field of soldering technology, in particular with the use of SMDs (Surface Mounted Devices), and here in turn in particular with so-called BGAs (Ball Grid Arrays), chip scale packages (CSPS) and Flip Chips (FCs), the problem arises that because of the small gap height between the underside of the components and the printed circuit board the quality of the soldered joint both of the outer and of the inner pin arrays with the corresponding contact points of the printed circuit board can no longer be checked merely by visual inspection. The corresponding electric or electronic components or assemblies are therefore in general subjected to an electric function test after the soldering. This is first of all, however, time-consuming and therefore expensive and can secondly only supply information as to whether the soldered joints conduct current or whether open or short-circuits occur. Information on the quality and hence solidity of the individual soldered joints and expected life-time cannot be supplied by this test method.

It is further known to check soldered joints non-destructively by means of x-rays. With this known method also it is possible in the end to check only undesirable soldering jumpers between adjacent pins, which cause a short-circuit, or the correct position of the pins of the components on the contact points of the printed circuit board; a statement on the quality of the individual soldered joints or the visual quality of the surface of the individual soldered joints or for example on undesirable flux residues in the area of the solderings is not possible. In addition such units are very expensive to procure and maintain and the application of this known method is not completely risk-free in terms of exposure to radiation. Furthermore, such units can only be operated by highly trained and specialized persons.

A further known method for determining the quality of a soldered joint is the production of a micrograph in cross-section through the respective soldered joint. Although it is certainly possible in this way to obtain reliable information on the quality of the soldered joint, for example on sufficient melting of the solder point of the component and hence satisfactory wetting of the contact point on the printed circuit board, a destructive test method is nevertheless involved here, which can be used only on a random sample basis for the drawing of conclusions on the operating parameters of the soldering process. Moreover, a visual inspection of the surface of the individual soldered joints is also not possible in this case.

Finally, there are known from the field of medicine and engineering endoscopes with illuminating devices, with which inaccessible areas can be inspected visually. The known endoscopes have a substantially tubular layout, at the axially outer end of which a deflection unit with illumination is disposed, which deflects the light exiting out of the tubular arrangement in the gap direction or deflects the gap image in the direction of the ocular. Because of its type of construction, however, viewing into gaps of small height, in particular in the range below 1 mm gap height, as is regularly the case in particular with BGAs and other SMDS, is not possible.

SUMMARY AND OBJECTS OF THE INVENTION

Starting from this prior art it is the object of the present invention to create a generic apparatus which permits the visual inspection of in particular concealed soldered joints nondestructively in a comparatively simple and cost-effective manner.

According to the invention, an apparatus for the visual inspection of concealed soldered joints, between an electric or electronic component disposed on the surface of a printed circuit board and the printed circuit board, is provided with an ocular unit, a lens head, an image transmission unit for transmitting the image received by the lens head to the ocular unit and an illuminating device for illuminating the soldered joints to be tested. The lens head comprises a device for image deviation which extends up to the axially outer end of the lens head. The illuminating device is disposed in the lens head in such a way that the exit angle of the light of the illuminating device out of the lens head is substantially equal to the deviation angle of the image deviation. The exit point of the light is disposed next to the device for image deviation in the area of the axially outer end of the lens head.

It is also a further object of the invention to provide a method with which the quality of a soldered joint between an electric or electronic component disposed on the surface of a printed circuit board or similar, in particular an SMD or BGA component, and the printed circuit board is checkable in a simple manner.

According to the invention the apparatus for the visual inspection of concealed soldered joints comprises, in particular between an electric or electronic component soldered to a printed circuit board, for example a BGA, and the printed circuit board, for the checking of the quality of the soldered joint, first and foremost an ocular unit, a lens head, an image transmission unit for transmitting the image received by the lens head to the ocular unit and an illuminating device for illuminating the soldered joints to be tested. In other words, the apparatus according to the invention comprises first and foremost the basic constructional form of an industrial or medical endoscope. Further there is provided in the area of the lens head in a manner first and foremost also known per se a device for image deflection.

In contrast to the known endoscopes, however, in which the lens or the deflection device is by virtue of the type of construction located at least a short distance from the axially outer "distal" end of the lens head, with the apparatus according to the invention the device for image deflection extends up to the axially outer end of the lens head. For this reason alone the image exit or image entry point of the lens can be placed considerably closer to the printed circuit board in comparison with the prior art, so that gaps of smaller height or soldered joints disposed therein are visually inspectable.

Likewise in contrast to the known endoscopes, in which the illuminating device or the light exit is disposed above or below the lens or the deflection unit, whereby the gap height to be reached visually is increased and/or an undesirable light shadow is generated in the gap area, according to the invention the illuminating device is disposed in the lens head in such a way that the exit angle of the light of the illuminating device from the lens head is substantially equal to the deviation angle of the image deviation and the exit point of the light is disposed next to the device for image deviation in the vicinity of the axially outer end of the lens head. This means in other words that on the one hand the illuminating device is disposed at substantially the same height, referred to the printed circuit board surface or gap plane, as the image exit or image entry point of the lens and on the other the image illumination takes place without any vertical shading.

Overall, soldered joints in gaps with a height of less than 1 mm and well below this can be inspected visually in a simple manner with the apparatus according to the invention. This means in particular that the individual soldered joints for example in BGAS, CSPs or FCs which as a rule have a gap height of approx. 0.02 to 0.8 mm between component underside and printed circuit board, are visually checkable nondestructively for soldering defects, undesirable jumper formation, contaminations and similar.

In basically any manner the exit of the light of the illuminating device can take place monolaterally at the lens head. According to a preferred embodiment of the invention, however, the exit of the light of the illuminating device from the lens head takes place bilaterally next to the device for image deflection, whereby a regular illumination of the field of view is ensured.

The deflection or deviation of the image in the lens head from the direction of the object to be observed in the direction of the ocular can likewise take place in any manner, for example in the simplest case by means of a deviating mirror. Preferably, however, the device for image deviation comprises a deviating prism, in which the deviation takes place in manner known per se. In comparison with mirror deviation, therefore, in particular the visual quality of the image can be improved and in particular also the image exit or image entry point of the lens be moved further downwards, namely in the direction of the axially outer end of the lens head.

The deviation angle of the device for image deviation is basically arbitrary and can lie between 0 and 180 degrees. The deviation angle further depends substantially on the angle at which the endoscope of the apparatus is positioned relative to the printed circuit board surface. Preferably the deviation angle comes to substantially 90 degrees. This means in other words that the apparatus according to this embodiment of the invention is, referred to the optical axis between lens and ocular, positioned substantially at right angles to the printed circuit board and hence to the gap plane. The apparatus can therefore also be used with densely equipped printed circuit boards and hence comparatively narrow gaps between the components to be checked.

In particular if it is not only the outer soldered joints in the edge area of the component that have to be checked, the lens is according to a further particularly preferred embodiment of the invention constructed in such a way that the depth of field area of the image or the focus distance correspond to at least half the component size, for example half the component width, half the component length or half the component diameter. In this way the whole of the gap interior can be checked visually by the inspection of mutually opposite sides of the component. The depth of field area of the lens can further be pre-set in manner known per se for example through the focal length of the lens.

According to a particularly preferred embodiment the lens head comprises a housing with at least one laterally open recess tapering towards the axially outer end of the lens head and bounded on both sides by flange-type webs. The deviating prism or the deviating mirror is disposed in this housing in such a way that the free surface of the deviating prism, i.e. that facing the gap, or the mirror surface in the recess faces outwards, referred to the housing and the recess, and the lower lateral edge of the deviating prism or the deviating mirror seals the lens head towards the axially outer end. This means in other words that the lower end of the deviating prism or the deviating mirror can be brought to rest directly against the printed circuit board, in order to guarantee an image deviation also into extremely low gaps, while the lateral edges of the prism or the mirror are protected against damage by the flange-type webs and the prism or the mirror is simultaneously fixable by these webs. In this embodiment the light exits of the illuminating device can further be disposed in the flange-type webs.

According to a further preferred embodiment the illuminating device comprises at least one glass fiber bundle which is connectable with its first axial end to a light source, whether the latter be disposed externally or else in or on the apparatus, and forms with its second axial end the light exit of the illuminating device on the lens head. There can be achieved in simple manner by the use of a glass fiber bundle in particular a light exit which, if there is adequate illumination intensity, has a sufficiently small diameter for illuminating a narrow gap. If two or more light exits are provided in the lens head, the respective glass fiber bundles can be combined into one bundle between light exit and light source and be fed to a common light source.

The transmission of the gap image from the lens head to the ocular can take place for example by means of a lens or mirror system. Preferably however the apparatus according to the invention comprises for the image transmission at least one further glass fiber bundle, which can be coupled optically with its first end to the unit for image deviation, in particular the deviating prism, and with its second end to the ocular.

In principle all kinds of soldering defects can be checked and determined visually with the embodiments described above, both those in the edge area and, if there is a sufficient depth of field of the lens, in the inner area of the soldering field for example of a BGA. In particular, but by no means exclusively, if undesirable soldering jumpers causing a short circuit are to be detected, namely jumpers between adjacent "solder pins" of a BGA, CSP or FC with a large number of soldering points, a second illuminating device is provided according to a particularly preferred embodiment of the invention, which is positionable opposite the lens head substantially in the viewing or in the image direction of the apparatus, referred to the gap plane, and illuminates in the direction of the lens head. It is thus possible in a simple manner, with viewing through the gap intervals between the individual rows of the soldering points, for a short-circuit jumper to be eliminated by recognition of the counterlight source and, conversely, for an undesirable jumper to be determined in an unambiguous manner if the counterlight source cannot be seen.

According to a further embodiment of the invention the second illuminating device comprises a counterlight head with a housing with at least one laterally open recess tapering towards the axially outer end of the counter-light head, wherein in the housing a deviating prism or a deviating mirror, which is connectable to a light source via a glass fiber bundle, is disposed in such a way that the free surface of the deviating prism or the mirror surface in the recess faces outwards and the lower lateral edge of the deviating prism or of the deviating mirror seals the counterlight head towards the axially outer end. This means in other words that the light deviation and the light exit take place via the prism, which in this embodiment does not have an image-transferring function of any kind. Because of the previously described shape the prism and hence the light exit can again be placed close to the surface of the printed circuit board and therefore in the gap plane.

According to an alternative embodiment to the latter the second illuminating device can comprise a counterlight head which is of substantially identical construction to the lens head of the apparatus. In this embodiment the counterlight head and the lens head can respectively serve simultaneously or alternately as an illuminating device and/or image detector, so that simultaneously or alternately the gap can be checked from both sides for example of a BGA. To this end the prism of the counterlight head can be couplable reversibly with the ocular of the lens head or else with a separate ocular.

In particular if the counterlight head serves simply as a counterlight source, according to a further embodiment of the invention the glass fiber bundle at least of the second illuminating device can run in a flexible spiral tube. In this way firstly the glass fiber bundle is reliably protected against mechanical damage and secondly the counterlight head can thereby in conformance with BGAs of varying dimensions be adjusted in particular as regards its distance from the lens head.

The illuminating device of the counterlight head and the illuminating device of the lens head can be coupled to different light sources in any manner. Preferably, however, the glass fiber bundles of the lens head and of the counter-light head are connectable to the same light source. An overall structural layout which is simple and cost-effective is thereby obtained.

According to a further embodiment the first and/or the second illuminating device or the light source of the first and/or second illuminating device can be adjustable in their luminous strength or light intensity.

It is of critical importance for the invention that the lens head is illuminatable by the counterlight source. To this end the lens head and the second illuminating device are preferably couplable via a linkage, rack or similar such that an exactly defined relative position of lens head and illuminating device, in particular counterlight head, is adjustable.

According to a particularly preferred embodiment the linkage or rack comprises for this purpose a freely projecting bracket which is fixable substantially rigidly to a housing section of the apparatus between lens head and ocular or is part of said housing section. In this embodiment the bracket comprises, displaceable in longitudinal direction in a guide element, a holding device in which the second illuminating device is fixable indirectly or directly and with which in particular the axial distance between lens head and counterlight head is adjustable.

The image of the gap or of the soldered joints disposed therein which is transmitted by the lens to the ocular can be inspected directly by an observer at the ocular. According to a preferred embodiment, however, an image-recording, image-converting and/or image-processing device of an electronic, magnetic or optical kind is couplable indirectly or directly in the vicinity of the ocular. This can be for example a video or television camera whose CCD image sensor is connectable to the ocular directly or indirectly via a corresponding lens. The video image so received can be passed to a screen and/or be subjected to an image processing in a computer. The checking of soldered joints beneath a BGA can thereby be automated in basically any manner for example by comparison of the image with reference images. Furthermore, the standoff height or gap can be measured directly on a video screen or by a program of a computer to detect a critical height which can be a measure of the quality of the soldered joint.

The apparatus according to the invention can in manner known per se be disposed on an X-Y table on which a printed circuit board-component soldered joint to be investigated can be brought into the test position below the apparatus or, conversely, the apparatus can be brought into the test position above the printed circuit board-component soldered joint.

According to the invention the apparatus described above can in a particularly advantageous manner be used in a method for checking the quality of the soldered joint between an electrical or electronic component arranged on the surface of a printed circuit board or similar, in particular an SMD, BGA, CSP or FC component, and the printed circuit board. The component to be investigated in terms of the soldered joint with the printed circuit board comprises, arranged in rows and gaps after the manner of a matrix, a large number of solder pins or solder points which are solderable with a corresponding number of contact points complementary as to shape and function disposed on the printed circuit board. The method according to the invention comprises the following method steps:

a) In a first method step first of all a visual examination is made of the soldered joints of the outermost row of soldered joints of a first side of the component to be tested, wherein the component is moved stepwise according to the spacing of the solder point rows or gaps past the lens head of the apparatus or, conversely, the lens head of the apparatus is moved step-wise past the component. It is not absolutely necessary for all the solder points to be checked here; instead, a comparatively reliable finding on the overall quality of the soldering can be obtained simply by checking of the corner soldering points. Moreover, use can be made, in evaluating the quality of the soldered joint, both of the surface of the soldered joint, in particular also flux residues, and for example the geometrical form of the solder point, in particular the "crowning" at the solder points of a BGA as a measure of a sufficient melting during the soldering process and the coplanarity of component and printed circuit board. The distance or the standoff height of the component underside from the printed circuit board surface can be a further measure of the quality of the soldered joint or at least of sufficient melting of the solder points during the soldering process. The latter can easily be measured as the gap height with an apparatus according to the invention.

b) In further method steps the component or the apparatus is rotated respectively through 90 degrees, wherein a visual examination is subsequently made in each case of the outermost rows of soldered joints of the further sides of the component analogously to method step a).

c) For the reliable determination of undesirable jumpers between neighboring solder pins, which can lead to electrical failure of the component, there takes place according to the invention in a further method step a visual examination of the channels formed between the respective gaps or rows for optical visibility.

Method steps a) to c) do not necessarily have to be carried out in this time sequence. Instead method step c) in particular can be carried out at the same time as method steps a) and b) during the step-wise moving of the component past the lens head or, conversely, the lens head past the component.

According to a preferred embodiment method step c) is carried out with counterlight, whereby a particularly easy and fast recognition of undesirable short-circuit jumpers is obtained.

In order to fully check a component or the soldered joints between the component and the printed circuit board, with method steps a) and b), at the same time or staggered in time, the soldered joints of the inner rows can be checked visually for soldering defects by viewing into the channels formed between the gaps or rows. In particular co-planarity defects between component and printed circuit board in the gap interior can thereby be determined easily and reliably.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENT

Figure 1:
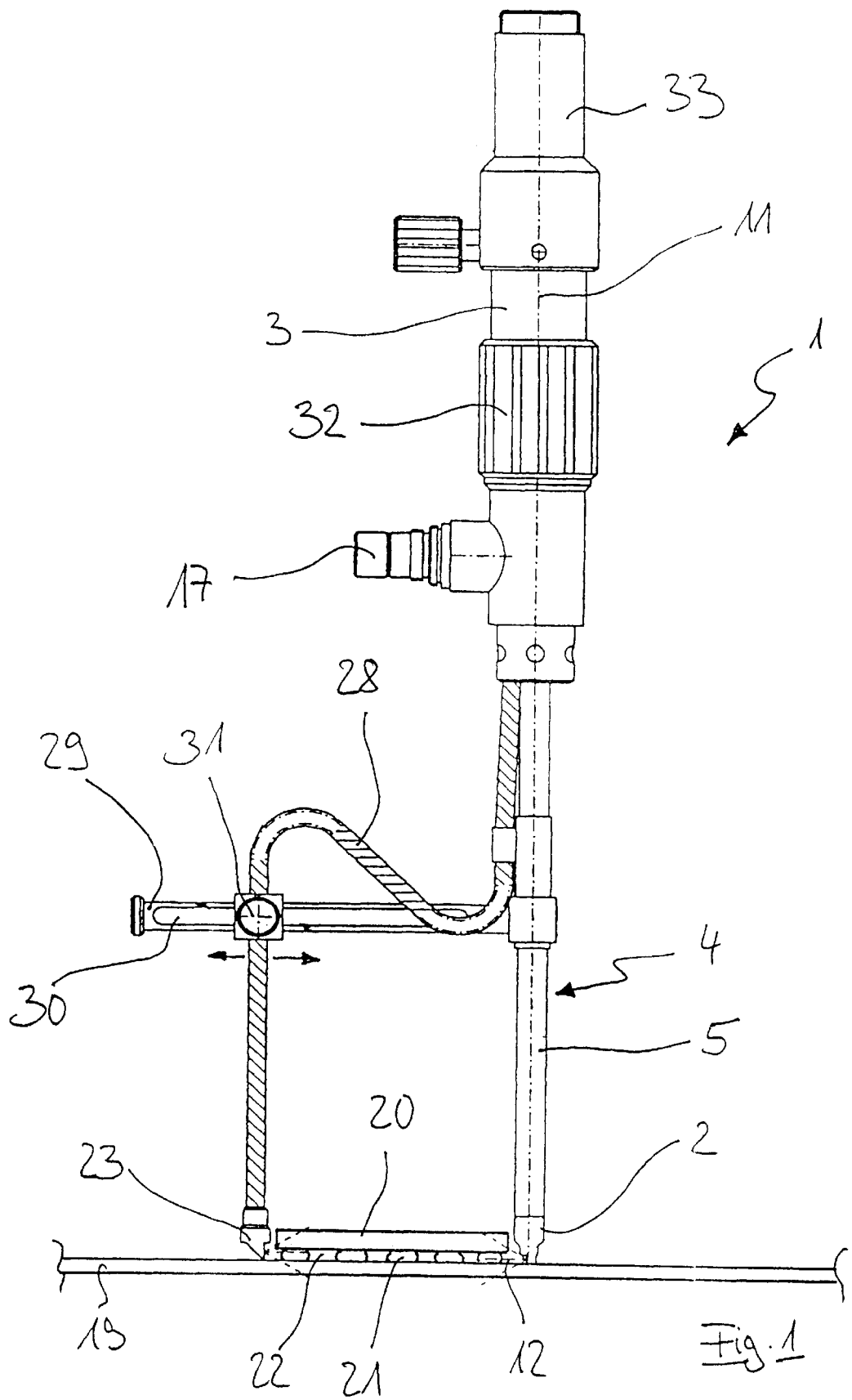
FIG. 1 is a diagrammatic representation of an embodiment of the apparatus according to the invention in elevation.

The apparatus 1 according to the invention shown in FIG. 1 has substantially the outer form of an endoscope. The apparatus 1 is further fitted with a lens head 2, which in manner known per se contains a lens, an ocular unit 3 and an image transmission unit 4 for transmitting the image received by the lens head 2 to the ocular unit 3. The image transmission unit 4 is disposed in a substantially tubular housing section 5 of the apparatus 1 and comprises a glass fiber bundle 18 indicated only diagrammatically in the view according to FIG. 2, which couples the lens head 2 with the ocular unit 3 visually, that is to say transmitting an image. As an alternative, there may be a series of lenses between the lens head 2 and the ocular unit which transmit and eventually magnify the image.

Figure 2:
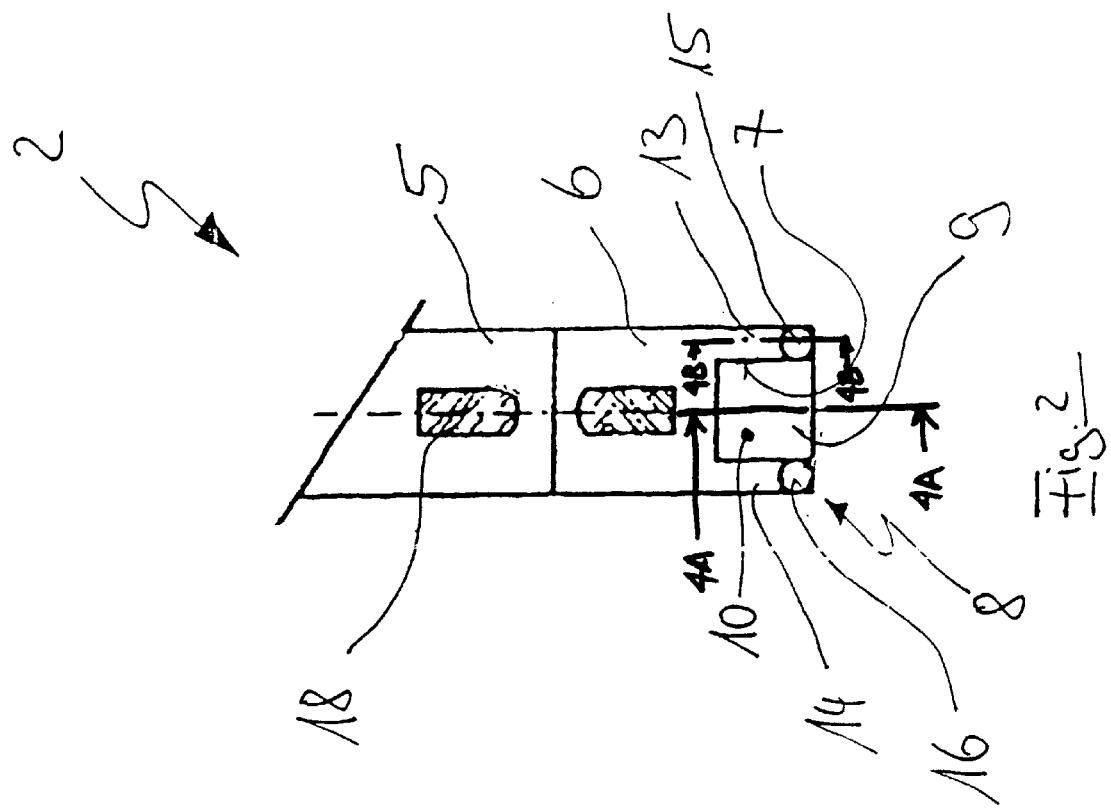
FIG. 2 is an enlarged diagrammatic partly cut-away view of the lens head of the embodiment according to FIG. 1, wherein the lens head is rotated through 90 degrees compared with the view according to FIG. 1.

The lens head 2, which is shown enlarged in FIG. 2, comprises a housing 6, preferably of stainless steel, which is formed funnel-shaped in cross section (cf. FIG. 1). The housing 6 is provided with a recess 7, which in the view according to FIG. 2 is substantially square-shaped. The recess 7 is further open both downwards, that is to say towards the axially outer end 8 of the apparatus 1, and laterally, that is to say towards the observer in the view according to FIG. 1. In the recess 7 a deviating prism 9 is disposed in such a way that the free prism face 10 faces outwards (to the left in the view according to FIG. 1) and a deviation or deflection of the optical path by 90 degrees takes place out of the vertical axis 11 formed by ocular unit 3 and lens head into the horizontal axis 12 and vice-versa.

The recess 7 is bounded laterally by two flange-type webs 13 and 14. These webs serve firstly for the fixing and for the protection of the deviating prism 9 against mechanical damage and secondly light exits 15 and 16 which are part of an illuminating device are disposed in the axially outer ends of the webs 13 and 14. The light exits 15 and 16 are in this embodiment formed by the free axial ends respectively of a glass fiber bundle, which free axial ends are led through the lens head 2 and the housing section 5 to a glass fiber connection 17 which serves for the feeding of the light of a light source (not shown), so that both light exits 15 and 16 are fed from the same light source. The glass fiber bundles are so oriented in the vicinity of the light exits so that the exit angle of the light is substantially equal to the deviation angle of the image deviation, whereby the whole of the visually attainable field of view is illuminatable without any vertical shadowing.

In FIG. 1 the apparatus 1 according to the invention, more precisely the lens head 2, is placed as normal on a printed circuit board or held only a short distance above the printed circuit board surface. There is fixed to the printed circuit board in known manner an electronic component 20 in the form of a BGA (Ball Grid Array) by soldering via the solder points 21. The gap 22, shown with enlarged thickness not to scale, between the component underside and the printed circuit board surface has as a rule a gap height of between 0.02 and 0.8 mm. By virtue of the features of the invention which are described above, in particular the arrangement of the deviating prism 9 directly up to the axially outermost distal end of the lens head 2, the image exit or image entry point of the prism and hence of the lens as a whole can be moved into the gap area, whereby the gap and hence the interior soldered joints disposed therein are visually accessible, wherein moreover, because of the light exit at substantially the same axial height, or longitudinal position, above the printed circuit board surface as the image exit or image entry point, sufficient illumination and hence good observability is ensured in the gap area.

As shown in FIG. 2, the deviating prism 9 is receivable of the external image over a longitudinal or axial image distance which extends from the bottom to the top of prism 9 in FIG. 2. The light exits 15, 16 emit the light at a position within this longitudinal image distance. The longitudinal image distance has one longitudinal or axial end at a farthest longitudinal distance of the lens head 2, which is the bottom of lens head 2 and prism 9 in FIG. 2. The light exits 15, 16 emit the light at a position adjacent this farthest longitudinal distance.

Figure 3:
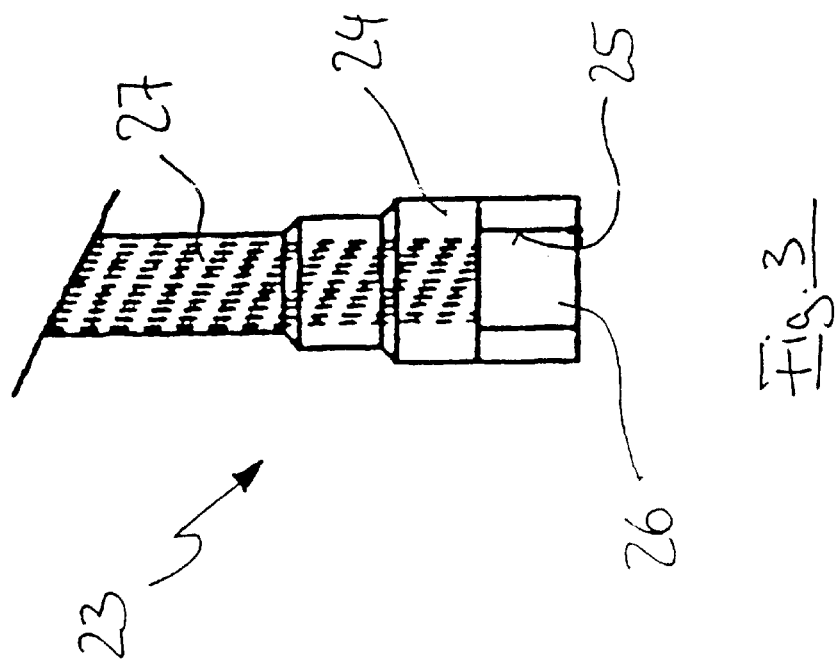
FIG. 3 is an enlarged diagrammatic view corresponding to FIG. 2 of the counterlight head of the apparatus according to the invention.
Figure 4A:
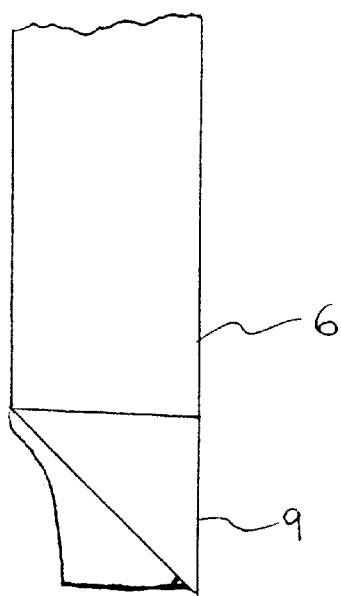
FIG. 4a is a sectional view taken along line 4a—4a of FIG. 2.
Figure 4B:
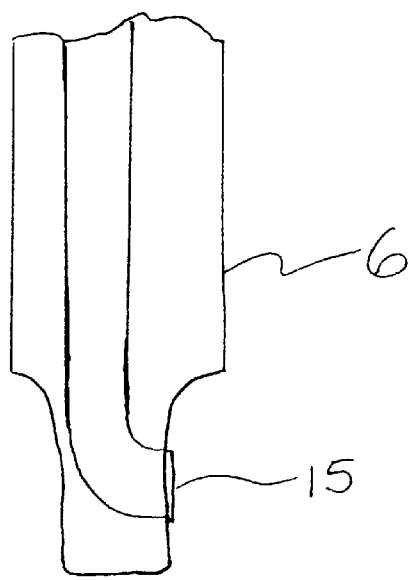
FIG. 4b is a sectional view taken along line 4b—4b of FIG. 2.

The embodiment of an apparatus 1 according to the invention which is shown in FIG. 1 is further equipped with a counterlight head 23. The counterlight head 23 comprises a housing 24 (cf. FIG. 3) which is provided in analogous manner to the housing 6 of the lens head 2 with a recess 25 and a deviating prism 26 disposed therein as described above for the lens head 2. In contrast to the lens head 2, however, the deviating prism 26 is combined visually not with the ocular unit 3, but rather via a glass fiber bundle 27, which is accommodated in a flexible spiral tube 28, in particular of stainless steel, with the glass fiber connection 17 and hence with the same light source (not shown) as the illuminating device of the lens head 2. The deviating prism 26 serves in particular for the introduction, directed substantially onto the lens head 2, of counterlight into the gap 22.

In the area of the housing section 5 a freely projecting bracket 29 is fixed to the apparatus 1. A groove-type guide element 30 is moreover formed in the bracket 29, in which a clamping member 31 is accommodated so as to be displaceable axially, that is to say in axial direction of the bracket 29, and fixable by clamping. The glass fiber bundle 27 running in the spiral tube 28 is held in the clamping member 31, so that with the displacement of the clamping member 31 the counterlight head 23 is simultaneously displaceable in the direction of the arrow and hence the exact distance between counterlight head 23 and lens head 2 is adjustable in particular in conformance with BGA components of differing sizes. Moreover, the bracket 29 may be adjusted vertically and rotated for at least 90° with respect to the housing section 5 to bring the bracket and combined therewith the counterlight 23 in a position of non-operation when not needed and vice versa.

In the area of the ocular unit 3 the apparatus 1 is provided with a focusing device 32 for the focusing of the optical image. In addition there is coupled optically to the ocular unit 3 a video camera 33 in order to supply the gap image received to an optical image processing device or image storage device. Furthermore, there may be arranged a TV-Zoom adaptor between the camera and the ocular unit to magnify the image transmitted.

While a specific embodiment of the invention has been shown and described in detail to illustrate the application of the principles of the invention, it will be understood that the invention may be embodied otherwise without departing from such principles.

What is claimed is:

1. An apparatus for the visual inspection of soldered joints between an electric or electronic component disposed on the surface of a printed circuit board and the printed circuit board, the apparatus comprising:
   an ocular unit;
   a lens head;
   an image transmission unit for transmitting the image received by said lens head to said ocular unit; and
   an illuminating device for illuminating the soldered joints to be inspected, said lens head comprising a device for image deflection extending up to an axially outermost end of said lens head, said illuminating device being disposed in said lens head to provide a light exit directed toward the soldered joints to be inspected, said light exit being disposed besides said device for image deflection at the axially outer end of said lens head.

2. The apparatus according to claim 1, wherein said light exit of the light of the illuminating device from the lens head is a bilateral exit next to the device for image deflection.

3. The apparatus according to claim 1, wherein the device for image deflection comprises at least one deviating prism or at least one deviating mirror.

4. The apparatus according to claim 1, wherein the deviation angle of the device for image deflection is between 0 and 180 degrees.

5. The apparatus according to claim 4, wherein the deviation angle of the device for image deflection is substantially 90 degrees.

6. The apparatus according to claim 1, wherein the lens head has a focal length such that the depth of field area of the image corresponds to at least half of a largest component size of the component on the printed circuit board.

7. The apparatus according to claim 1, wherein the lens head comprises a housing with at least one laterally open recess tapering towards the axially outer end of the lens head and bounded on both sides by flange-type webs, wherein a deviating prism or deviating mirror is disposed in the housing to cause a free surface of the deviating prism or the mirror surface in the recess faces outwards and the lower lateral edge of the deviating prism or of the deviating mirror seals the lens head towards the axially outer end, and wherein further the light exits of the illuminating device are arranged in the flange-type webs.

8. The apparatus according to claim 1, wherein the illuminating device comprises at least one glass fiber bundle with first and second ends, said first axial end is connectable to a light source and forms with said second axial end the light exit of the illuminating device on the lens head.

9. The apparatus according to claim 1, wherein the image transmission unit comprises at least one glass fiber bundle which is optically couplable with its first end to the unit for image deflection, and with its second end to the ocular unit.

10. The apparatus according to claim 1, wherein a second illuminating device, positionable substantially in a viewing direction of the apparatus opposite the lens head, illuminates in the direction of the lens head.

11. The apparatus according to claim 10, wherein the second illuminating device comprises a counterlight head with a housing with at least one laterally open recess tapering towards the axially outer end of the counterlight head, wherein in the housing a deviating prism or a deviating mirror, which is optically couplable to a light source via a glass fiber bundle, is disposed with the free surface of the deviating prism or the mirror surface in the recess facing outwards and the lower lateral edge of the deviating prism or of the deviating mirror seals the counterlight head towards the axially outer end.

12. The apparatus according to claim 11, wherein the glass fiber bundle of the lens head and of the counterlight head are connectable to the same light source.

13. The apparatus according to claim 10, wherein the second illuminating device comprises a counterlight head which is of substantially identical construction to the lens head.

14. The apparatus according to claim 10 wherein the glass fiber bundle at least of the second illuminating device runs in a flexible spiral tube.

15. The apparatus according to claim 10, wherein the lens head and the second illuminating device are couplable via a linkage or rack to provide an exactly defined relative position of lens head and second illuminating device is adjustable.

16. The apparatus according to claim 15, wherein the linkage or rack comprises a freely projecting bracket which is fixable substantially rigidly to a housing section of the apparatus between lens head and ocular unit or is part of the housing section, wherein the bracket comprises, displaceable in longitudinal direction in a guide element, a holding device in which the second illuminating device is fixable, with which the axial distance between lens head and counterlight head is adjustable.

17. A method for checking the quality of the soldered joint between an electric or electronic component disposed on the surface of a circuit board including an SMD, BGA, CSP or FC component, and the circuit board, the method comprising the steps of:
   using an ocular unit with an apparatus including a lens head, an image transmission unit for transmitting the image received by the lens head to the ocular unit and an illuminating device for illuminating the soldered joints to be tested, in which the lens head comprises a deviating prism for image deflection which extends up to the axially outermost end of the lens head, and in which the illuminating device is disposed in the lens head to cause the exit angle of the light of the illuminating device out of the lens head is substantially equal to the deviation angle of the image deflection and the exit point of the light is disposed next to the deviating prism for image deflection in the area of the axially outer end of the lens head, the component comprising, arranged in rows and gaps after the manner of a matrix, a large number of solder pins, solder balls or solder points which are solderable with a corresponding number of contact points complementary as to shape and function disposed on the printed circuit board;

visually examining the soldered joints of the outermost row of soldered joints of a first side of the component to be tested with the ocular unit, wherein the component is moved step-wise according to the spacing of the solder joint rows or gaps past the lens head of the ocular unit or, conversely, the lens head of the ocular unit is moved step-wise past the component;

rotating of the component or the ocular unit through respectively 90 degrees and visually examining the soldered joints of the outermost rows of soldered joints of the further sides of the component with the ocular unit wherein the component is moved step-wise according to the spacing of the solder joints past the lens head of the ocular unit or, conversely, the lens head of the ocular unit is moved step-wise past the component; and visually examining the channels formed between the respective gaps or rows for optical visibility.

18. The method according to claim 17, wherein said visually examining the channels is performed with a counterlight.

19. The method according to claim 17, wherein in addition to said visually examing the soldered joints and said rotating the soldered joints of the inner rows are examined visually for soldering defects by viewing into the channels formed between the gaps or rows.

20. An apparatus for the visual inspection of soldered joints disposed between an electric or electronic component and a substrate, the apparatus comprising:

an ocular unit;

a lens head;

an image transmission unit for transmitting the image received by said lens head to said ocular unit, said ocular unit, said image transmission unit and said lens head being connected to form an assembly with said lens being at an end of said assembly to define an axial extent of said assembly; and an illuminating device for illuminating the soldered joints disposed between the electric or electronic component and the substrate, said lens head comprising an image deflection device for changing the direction of the image path from an incoming direction from between the electric or electronic component and the substrate to an outgoing direction, said image deflection device extending up to an axially outermost end of said lens head and up to said axial extent of said assembly, said illuminating device having a light exit to provide a light exit direction substantially toward said incoming direction, said light exit of said illuminating device being disposed circumferentially besides said device for image deflection.

21. The apparatus according to claim 20, wherein said image deflection device changes the direction of the image path by an image deflection angle, said illuminating device having a light source and a light transmission path changing the direction of light from said light source to said light exit by an angle substantially equal to said image deflection angle.

22. A visual inspection apparatus comprising:

an image transmission unit having a longitudinal axis with first and second ends at opposite longitudinal ends, said image transmission unit transmitting an image from said first end to said second end along said longitudinal axis;

a head arranged at said first end of said image transmission unit, said head extending a predetermined distance from said first end of said imagine transmission unit;

an image deflection device arranged in said head and being receivable of an external image at an image axis angularly spaced from said longitudinal axis of said image transmission unit, said image deflection device being feedable of the external image into said first end of said image transmission unit substantially along said longitudinal axis, said image deflection device being receivable of the external image at substantially a farthest longitudinal distance of said head from said image transmission unit;

an illuminating device in said bead, said illuminating device emitting light substantially parallel to said image axis at a longitudinal position of said image deflection device.

23. An apparatus in accordance with claim 22, wherein:

said image deflection device is receivable of the external image over a longitudinal image distance;

said illuminating device emits the light at a position within said longitudinal image distance.

24. An apparatus in accordance with claim 23, wherein:

said longitudinal image distance has one longitudinal end at said farthest longitudinal distance of said head;

said illuminating device emits the light at a position adjacent said farthest longitudinal distance.

25. An apparatus in accordance with claim 22, wherein:

said head includes a web longitudinally extending along one side of said image deflection device, said web extending to said farthest longitudinal distance.

26. An apparatus in accordance with claim 25, wherein:

said head includes another web longitudinally extending along another side of said image deflection device, said another web extending to said farthest longitudinal distance.

27. An apparatus in accordance with claim 26, wherein:

each of said webs define an opening for emitting light from said illuminating device.

28. An apparatus in accordance with claim 22, wherein:

said head includes a web longitudinally extending along one side of said image deflection device, said web extending substantially to said farthest longitudinal distance.

* * * * *

(12) INTER PARTES REEXAMINATION CERTIFICATE (466th)
United States Patent
Cannon

(10) Number: US 6,580,501 C1
(45) Certificate Issued: Oct. 5, 2012

(54) APPARATUS AND METHOD FOR THE VISUAL INSPECTION IN PARTICULAR OF CONCEALED SOLDERED JOINTS

(75) Inventor: Mark Cannon, Karlsruhe (DE)

(73) Assignee: Ersa GmbH, Wertheim (DE)

Reexamination Request:
No. 95/000,028, Nov. 13, 2003

Reexamination Certificate for:
Patent No.: 6,580,501
Issued: Jun. 17, 2003
Appl. No.: 09/866,400
Filed: May 25, 2001

Related U.S. Application Data

(63) Continuation of application No. 09/394,732, filed on Sep. 13, 1999, now abandoned.

(30) Foreign Application Priority Data

Oct. 19, 1998 (DE) .................................. 198 47 913

(51) Int. Cl.
*G01M 11/08* (2006.01)
*H05K 13/08* (2006.01)
*G01N 21/88* (2006.01)
*H05K 13/00* (2006.01)

(52) U.S. Cl. ............... 356/237.1; 356/237.5; 356/241.4; 359/798

(58) Field of Classification Search .................. None
See application file for complete search history.

(56) References Cited

To view the complete listing of prior art documents cited during the proceeding for Reexamination Control Number 95/000,028, please refer to the USPTO's public Patent Application Information Retrieval (PAIR) system under the Display References tab.

*Primary Examiner* — Albert J Gagliardi

(57) ABSTRACT

An apparatus for the visual inspection in particular of concealed soldered joints is provided, in particular between an electric or electronic component disposed on the surface of a printed circuit board and the printed circuit board. The apparatus includes with an ocular unit, a lens head, an image transmission unit for transmitting the image received by the lens head to the ocular unit and an illuminating device for illuminating the soldered joints to be tested. The lens head includes a device for image deviation which extends up to the axially outer end of the lens head, and in which the illuminating device is disposed in the lens head in such a way that the exit angle of the light of the illuminating device out of the lens head is substantially equal to the deviation angle of the image deviation. The exit point of the light is disposed next to the device for image deviation in the area of the axially outer end of the lens head.

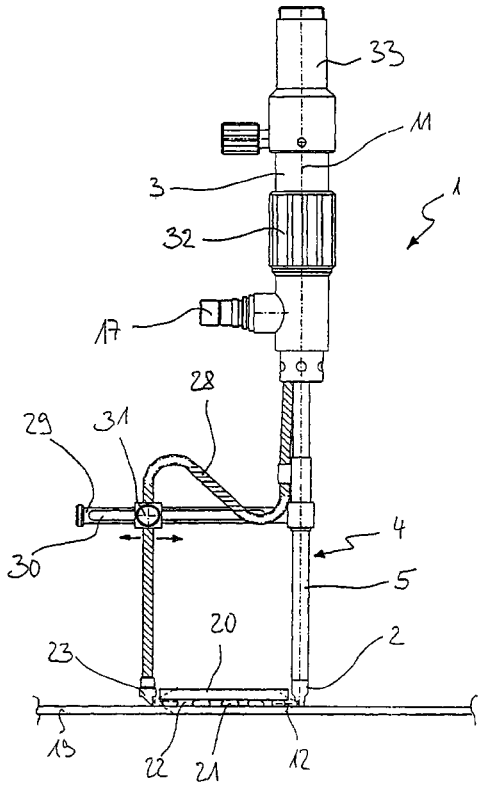

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-28 is confirmed.

New claim 29 is added and determined to be patentable.

*29. An apparatus for the visual inspection of soldered joints between an electric or electronic component disposed on the surface of a printed circuit board and the printed circuit board, the apparatus comprising:*

*an ocular unit;*
*a lens head extending to a lens head axial end at an axially outermost end of said lens head disposed adjacent to the surface of a printed circuit board;*
*an image transmission unit having a longitudinal axis, said ocular unit, said image transmission unit and said lens head being connected to form an assembly with a lens head end, at substantially a farthest longitudinal distance of said head from said image transmission unit, defining an axial extent of said assembly;*
*an illuminating device for illuminating the soldered joints to be inspected; and*
*image deflection means for receiving an external image at an image axis angularly spaced from said longitudinal axis of said image transmission unit, said image transmission unit including image transmission means for transmitting the image to said ocular unit, said image deflection means being supported by said lens head and extending to said lens head axial end, said illuminating device being disposed in said lens head to provide a light exit directed toward the soldered joints to be inspected, said light exit being disposed besides said image deflection means and emitting light substantially parallel to said image axis.*

\* \* \* \* \*